United States Patent
Klasek et al.

(10) Patent No.: US 8,459,259 B2
(45) Date of Patent: Jun. 11, 2013

(54) HEATING ELEMENT, HUMIDIFIER FOR RESPIRATORY APPARATUS INCLUDING HEATING ELEMENT, AND RESPIRATORY APPARATUS

(75) Inventors: Paul Jan Klasek, Bonnyrigg Heights (AU); Dieter Heidmann, Cherrybrook (AU)

(73) Assignee: ResMed Limited, Bella Vista (AU)

( * ) Notice: Subject to any disclaimer, the term of this patent is extended or adjusted under 35 U.S.C. 154(b) by 562 days.

(21) Appl. No.: 12/669,889

(22) PCT Filed: Jun. 30, 2008

(86) PCT No.: PCT/AU2008/000962
§ 371 (c)(1),
(2), (4) Date: Jan. 20, 2010

(87) PCT Pub. No.: WO2009/015410
PCT Pub. Date: Feb. 5, 2009

(65) Prior Publication Data
US 2010/0206308 A1  Aug. 19, 2010

Related U.S. Application Data

(60) Provisional application No. 60/952,899, filed on Jul. 31, 2007, provisional application No. 61/021,372, filed on Jan. 16, 2008, provisional application No. 61/059,410, filed on Jun. 6, 2008.

(51) Int. Cl.
*A61M 16/16* (2006.01)

(52) U.S. Cl.
USPC .............................. 128/203.27; 128/203.26

(58) Field of Classification Search
USPC ........................................ 128/203.26, 203.27
See application file for complete search history.

(56) References Cited

U.S. PATENT DOCUMENTS 3,638,926 A   2/1972   Melville et al.
3,659,604 A   5/1972   Melville et al.
(Continued)

FOREIGN PATENT DOCUMENTS

EP   0 205 072 A2   12/1986
EP   0 190 080 B1   5/1991
(Continued)

OTHER PUBLICATIONS

International Preliminary Report on Patentability mailed Feb. 2, 2010 in PCT/AU2008/000962.

(Continued)

*Primary Examiner* — Nicholas Lucchesi
*Assistant Examiner* — Gerald Landry, II
(74) *Attorney, Agent, or Firm* — Nixon & Vanderhye P.C.

(57) ABSTRACT

An apparatus for delivering breathable gas to a patient includes a flow generator to generate a flow of breathable gas; a humidifier chamber to contain a supply of water; a first flow path to deliver the flow of breathable gas from the flow generator to the humidifier chamber; a second flow path to deliver the flow of breathable gas from the humidifier chamber to a patient interface; and a wicking element and/or a flat, elongate heating element provided at least in the humidifier chamber. A method of delivering a flow of breathable gas to a patient includes generating a flow of breathable gas; and humidifying the flow by passing the flow over a supply of water. Humidifying the flow includes heating the supply of water and/or the flow with a heating element in thermal contact with the water and/or the flow before passing the supply of water, the flow over the supply of water, and/or the flow after passing the supply of water; and controlling a voltage applied to the heating element to control the humidity of the flow. A tube for use in delivering a flow of breathable gas to a patient includes a circuit including electrically conductive ink provided on an inner surface and/or an outer surface.

108 Claims, 16 Drawing Sheets

U.S. PATENT DOCUMENTS

| | | | |
|---|---|---|---|
| 3,954,920 A | 5/1976 | Heath | |
| 4,225,542 A | 9/1980 | Wall et al. | |
| 4,430,994 A | 2/1984 | Clawson et al. | |
| 4,601,287 A | 7/1986 | Royce, Jr. | |
| 4,618,462 A | 10/1986 | Fisher | |
| 4,621,633 A | 11/1986 | Bowles et al. | |
| 4,715,998 A | 12/1987 | Clow | |
| 4,967,744 A * | 11/1990 | Chua | 128/204.18 |
| 5,062,145 A | 10/1991 | Zwaan et al. | |
| 5,279,288 A * | 1/1994 | Christopher | 128/204.18 |
| 5,322,075 A | 6/1994 | Deevi et al. | |
| 5,428,206 A | 6/1995 | Uchida et al. | |
| 5,454,061 A | 9/1995 | Carlson | |
| 5,462,048 A | 10/1995 | Lambert et al. | |
| 5,537,996 A | 7/1996 | McPhee | |
| 5,592,933 A | 1/1997 | Zucchi | |
| 6,078,730 A * | 6/2000 | Huddart et al. | 392/480 |
| 6,095,505 A | 8/2000 | Miller | |
| 6,167,883 B1 * | 1/2001 | Beran et al. | 128/203.17 |
| 6,175,687 B1 | 1/2001 | Imamura et al. | |
| 6,349,722 B1 * | 2/2002 | Gradon et al. | 128/203.17 |
| 6,367,472 B1 | 4/2002 | Koch | |
| 6,766,817 B2 | 7/2004 | da Silva | |
| 6,770,848 B2 | 8/2004 | Haas et al. | |
| 6,976,489 B2 | 12/2005 | Mantell et al. | |
| 7,120,354 B2 * | 10/2006 | Mackie et al. | 392/480 |
| 7,285,255 B2 | 10/2007 | Kadlec et al. | |
| 7,647,925 B2 | 1/2010 | Mantell et al. | |
| 8,028,692 B2 * | 10/2011 | Ho | 128/200.24 |
| 2002/0124847 A1 | 9/2002 | Smith et al. | |
| 2004/0081784 A1 | 4/2004 | Smith et al. | |
| 2004/0149284 A1 * | 8/2004 | Smith et al. | 128/203.16 |
| 2004/0250815 A1 * | 12/2004 | Scott et al. | 128/204.17 |
| 2006/0283447 A1 * | 12/2006 | Dhuper et al. | 128/203.12 |
| 2008/0028850 A1 * | 2/2008 | Payton et al. | 73/204.19 |
| 2010/0083965 A1 * | 4/2010 | Virr et al. | 128/203.26 |

FOREIGN PATENT DOCUMENTS

| | | |
|---|---|---|
| EP | 1 122 982 B1 | 5/2003 |
| EP | 1 166 814 B1 | 12/2004 |
| EP | 1 530 980 A1 | 5/2005 |
| FR | 2 543 442 A1 | 10/1984 |
| GB | 2 173 107 A | 10/1986 |
| JP | 9-234247 A | 9/1997 |
| NZ | 226392 | 10/1992 |
| WO | WO 2004/002542 A1 | 1/2004 |
| WO | WO 2007/069922 A1 | 6/2007 |
| WO | WO 2008/055307 A1 | 5/2008 |

OTHER PUBLICATIONS

Unsolicited email from Elson Silva, PhD, dated Aug. 20, 2010, "Respecting Hydrology Science in the Patenting System", 4 pages.
New Zealand Examination Report mailed Mar. 1, 2012 in New Zealand Appln. No. 598371 (3 pages).
International Search Report mailed Sep. 12, 2008 in PCT/AU2008/000962.
New Zealand Examination Report Mailed May 20, 2011 in New Zealand Application No. 581899 (3 pages).

* cited by examiner

HEATING ELEMENT, HUMIDIFIER FOR RESPIRATORY APPARATUS INCLUDING HEATING ELEMENT, AND RESPIRATORY APPARATUS

CROSS REFERENCE TO RELATED APPLICATIONS

This application is the U.S. national phase of International Application No. PCT/AU2008/000962 filed Jun. 30, 2008 which designated the U.S. and claims priority to U.S. Application Nos. 60/952,899, filed Jul. 31, 2007, 61/021,372, filed Jan. 16, 2008, and 61/059,410, filed Jun. 6, 2008, the entire contents of each application being incorporated herein by reference.

FIELD OF THE INVENTION

The present invention relates to humidification and heater arrangements used to control the humidity of breathable gases used in all forms of respiratory apparatus ventilation systems including invasive and non-invasive ventilation, Continuous Positive Airway Pressure (CPAP), Bi-level therapy and treatment for sleep disordered breathing (SDB) conditions such as Obstructive Sleep Apnea (OSA), and for various other respiratory disorders and diseases.

BACKGROUND OF THE INVENTION

Respiratory apparatus commonly have means to alter the humidity of the breathable gas in order to reduce drying of the patient's airway and consequent patient discomfort and associated complications. The use of a humidifier placed between the flow generator and the patient mask, produces humidified gas that minimizes drying of the nasal mucosa and increases patient airway comfort. In addition in cooler climates, warm air applied generally to the face area in and about the mask, as may occur inadvertently by a leak, is more comfortable than cold air.

Many humidifier types are available, although the most convenient form is one that is either integrated with or configured to be coupled to the relevant respiratory apparatus. While passive humidifiers can provide some relief, generally a heated humidifier is required to provide sufficient humidity and temperature to the air so that patient will be comfortable. Humidifiers typically comprise a water tub having a capacity of several hundred milliliters, a heating element for heating the water in the tub, a control to enable the level of humidification to be varied, a gas inlet to receive gas from the flow generator, and a gas outlet adapted to be connected to a patient conduit that delivers the humidified pressurized gas to the patient's mask.

Typically, the heating element is incorporated in a heater plate which sits under, and is in thermal contact with, the water tub.

The humidified air may cool on its path along the conduit from the humidifier to the patient, leading to the phenomenon of "rain-out", or condensation, forming on the inside of the conduit. To counter this, it is known to additionally heat the gas being supplied to the patient by means of a heated wire circuit inserted into the patient conduit which supplies the humidified gas from the humidifier to the patient's mask. Such a system is illustrated in Mosby's Respiratory Care Equipment ($7^{th}$ edition) at page 97.

Such a heating method for the patient conduit may only provide poor heat transfer due to the wire locating itself along the conduit wall rather than in the main gas stream. A wire will also only give poor turbulent mixing due to its low profile. As a result heat transfer may be poor and the mixing of water vapor and gas may also be poor.

Alternatively the heating wire circuit may be located in the wall of the patient conduit. Such a system is described in U.S. Pat. No. 6,918,389.

U.S. Pat. No. 6,918,389 describes a number of humidifier arrangements for supplying low relative humidity, high temperature humidified gas to the patient. Some of these arrangements include pre- or post-heating of the gas to reduce the relative humidity.

WO 2007/019268 A1 discloses a low cost CPAP flow generator and humidifier assembly, including a heating element, which may be a ribbon heater, placed inside the tub of the humidifier. WO 2007/019628 A1 does not disclose that the heating element may be provided in portions of the assembly other than the humidifier tub, including, for example, the hoses or conduits.

None of these prior art devices provides an entirely satisfactory solution to the provision of comfortable humidified breathable gas to the patient, nor to ease of construction and hygiene requirements and to energy and patient comfort requirements at startup.

SUMMARY OF THE INVENTION

According to a sample embodiment of the invention, an apparatus for delivering breathable gas to a patient comprises a flow generator to generate a flow of breathable gas; a humidifier chamber to contain a supply of water; a first flow path to deliver the flow of breathable gas from the flow generator to the humidifier chamber; a second flow path to deliver the flow of breathable gas from the humidifier chamber to a patient interface; and a heating element extending through the first flow path, the humidifier chamber, and into the second flow path.

According to another sample embodiment of the invention, a method of delivering a flow of breathable gas to a patient comprises generating a flow of breathable gas; and humidifying the flow by passing the flow over a supply of water. Humidifying the flow comprises heating the flow with a heating element in thermal contact with a) the flow before passing the supply of water, b) the supply of water, and/or c) the flow after passing the supply of water.

According to a further sample embodiment of the invention, a humidifier comprises a tub to contain a supply of water; an inlet to receive a flow of breathable gas, the inlet configured to direct the flow over the supply of water to humidify the flow; an outlet connectable to a conduit; a wicking element provided extending from the tub and towards the outlet and/or the inlet; and a heating element extending from the inlet to the outlet. The heating element is configured to contact the supply of water.

According to another sample embodiment of the invention, an apparatus for delivering breathable gas to a patient comprises a flow generator to generate a flow of breathable gas; a humidifier chamber to contain a supply of water; a first flow path to deliver the flow of breathable gas from the flow generator to the humidifier chamber; a second flow path to deliver the flow of breathable gas from the humidifier chamber to a patient interface; and a flat, elongate heating element provided at least in the humidifier chamber.

According to a further sample embodiment of the invention, a method of delivering a flow of breathable gas to a patient comprises generating a flow of breathable gas; and humidifying the flow by passing the flow over a supply of water. Humidifying the flow comprises heating the supply of water and/or the flow with a heating element in thermal contact with the water and/or the flow before passing the supply of water, the flow over the supply of water, and/or the flow after passing the supply of water; and controlling a voltage applied to the heating element to adjust the humidity of the flow.

According to another sample embodiment of the invention, a tube for use in delivering a flow of breathable gas to a patient comprises a circuit comprising electrically conductive ink provided on an inner surface and/or an outer surface.

According to yet another sample embodiment of the invention, a method of disinfecting an apparatus for delivering breathable gas to a patient is provided. The apparatus comprises a flow generator to generate a flow of breathable gas; a humidifier chamber to contain a supply of water; a first flow path to deliver the flow of breathable gas from the flow generator to the humidifier chamber; a second flow path to deliver the flow of breathable gas from the humidifier chamber to a patient interface; and a flat, elongate heating element provided in the humidifier chamber, the first flow path, and/or the second flow path. The method comprises, prior to and/or after operation of the flow generator, heating the heating element to a temperature sufficient to kill bacteria and/or disinfect a wicking element.

According to still another sample embodiment of the invention, an apparatus for delivering breathable gas to a patient comprises a flow generator to generate a flow of breathable gas; a humidifier chamber to contain a supply of water; a first flow path to deliver the flow of breathable gas from the flow generator to the humidifier chamber; a second flow path to deliver the flow of breathable gas from the humidifier chamber to a patient interface; a wicking element provided at least in the humidifier chamber; a heating element extending through the first flow path, the humidifier chamber and into the second flow path; and a power supply and control configured to supply and control power to the heating element. The power supply and control is configured to supply and control power to the heating element prior to and/or after operation of the flow generator to heat the heating element to a temperature sufficient to kill bacteria and/or disinfect the wicking element.

BRIEF DESCRIPTION OF THE DRAWINGS

Sample embodiments of the invention will now be described with reference to the accompanying drawings, in which:

FIG. 18C illustrates an end view of a heating element according to FIGS. 18A and 18B;

DETAILED DESCRIPTION OF ILLUSTRATED EMBODIMENTS

Respiratory Apparatus with Heating Element

Figure 1:
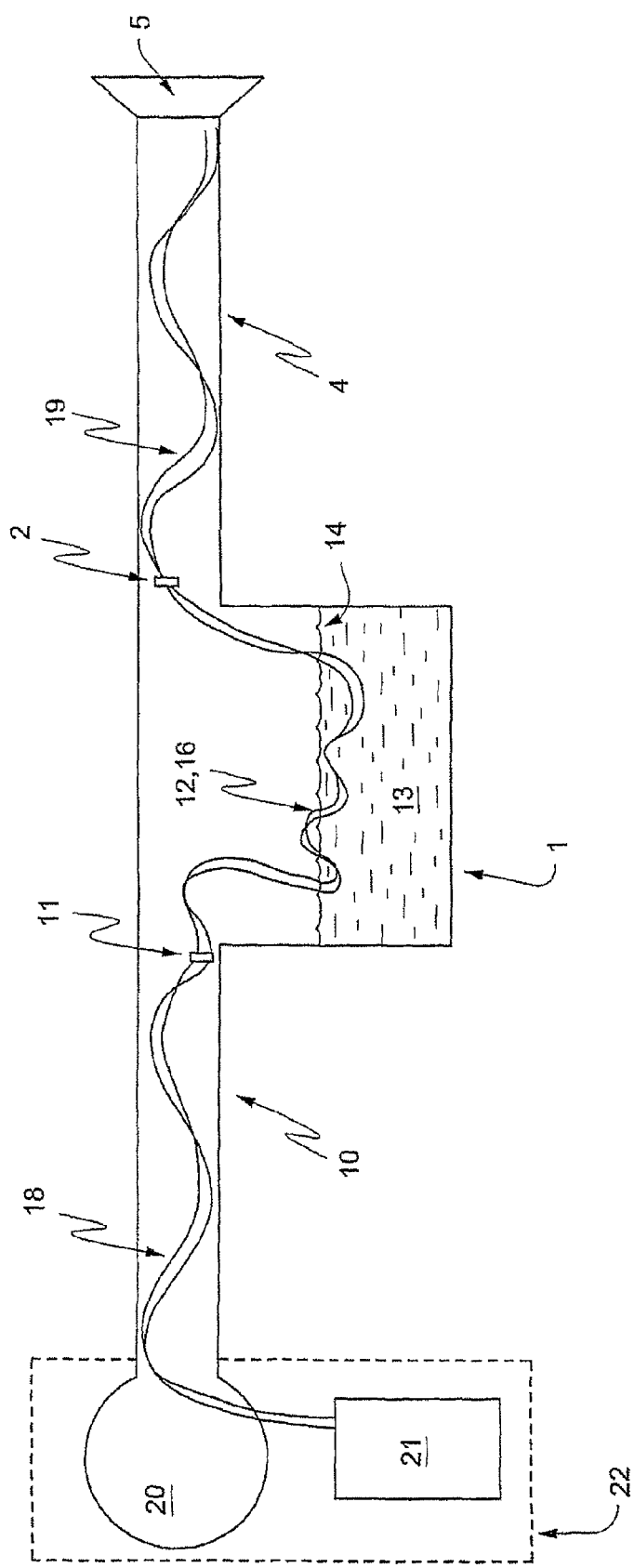
FIG. 1 schematically depicts a respiratory apparatus according to a sample embodiment of the invention.

Referring to FIG. 1, a respiratory apparatus according to a sample embodiment of the invention includes a flow generator 22, otherwise known as a positive airway (PAP) device which generates pressure suitable for respiratory therapy in the range of 2-30 cm $H_2O$. The flow generator 22 includes a blower 20 and a power supply and controller 21. As shown in FIG. 1, the blower 20 and the power supply and controller 21 may be incorporated into a single unit. However, it should be appreciated that the blower and the power supply and controller 21 may be provided separately.

The blower 20 provides a flow of breathable gas into an inlet conduit 10. The inlet conduit 10 is connected to an inlet 11 of a humidifier chamber 1. The humidifier chamber 1 includes water 13. The flow of breathable gas is forced over the surface 14 of the water 13 to vaporize a portion of the water to humidify the flow of breathable gas. The flow of breathable gas exits the humidifier chamber 1 at an outlet 2 into a patient conduit 4. The patient conduit 4 is connected to a patient interface 5, for example a mask.

A heating element 12, for example in the shape of a heating strip or ribbon, may be connected to the power supply and controller 21. The heating element 12 is provided through the inlet conduit 10 into the humidifier chamber 1. In the humidifier chamber 1, the heating element 12 is in contact with the water 13. It should be appreciated that the heating element 12 may only contact the surface 14 of the water 13, or that the heating element 12 may be submerged in the water 13, or portions of the heating element 12 may be submerged and other portions may be in contact with the surface 14 of the water 13. The heating element 12 exits the humidifier chamber 1 at the outlet 2 and extends into the patient conduit 4. The heating element 12 may extend through the patient conduit 4 up to the patient interface 5.

Heating Element First Embodiment

Figure 2:
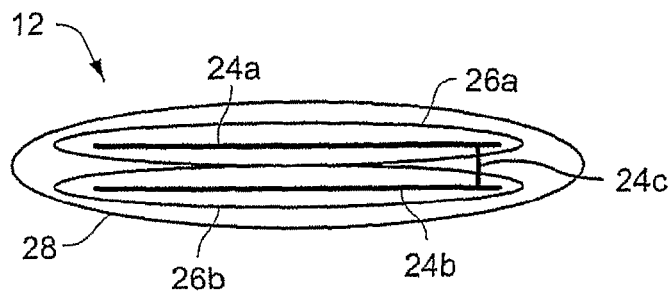
FIG. 2 schematically depicts a heating element according to a sample embodiment of the invention.

As shown in FIG. 2, the heating element 12 may comprise two resistive ribbon wires 24a, 24b. An insulating layer 26a, 26b is provided around each resistive ribbon wire 24a, 24b to provide dielectric insulation between at least two sections of the resistive ribbon wires 24a, 24b. The insulating layers 26a, 26b may be optionally encapsulated in a protective outer layer 28 to provide waterproofing and electrical safety requirements. The resistive ribbon wires 24a, 24b are electrically connected by a connection 24c, for example a spot weld, to provide an electrical connection to complete the circuit. The two ends 24d, 24e (FIG. 6) of the resistive ribbon wires 24a, 24b are exposed by removing portions of the insulating layers 26a, 26b (FIG. 7). The two ends 24d, 24e of the resistive ribbon wires 24a, 24b are connected to the power supply and controller 21 to provide a complete electrical circuit.

Heating Element Second Embodiment

Figure 3:
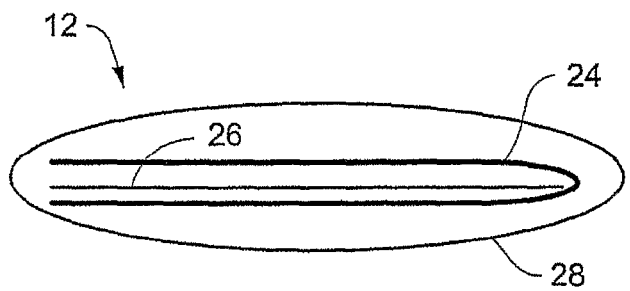
FIG. 3 schematically depicts a heating element according to a sample embodiment of the invention.

Referring to FIG. 3, in another sample embodiment, the heating element 12 is formed of a single length of resistive ribbon wire 24 that is bent in half. An insulating layer 26 is placed between the two halves of the bent resistive ribbon wire 24. The outer protective layer or coating 28 is then formed around the bent resistive ribbon wire 24, for example by shrink wrapping or dipping.

Heating Element Third Embodiment

Figure 4A:
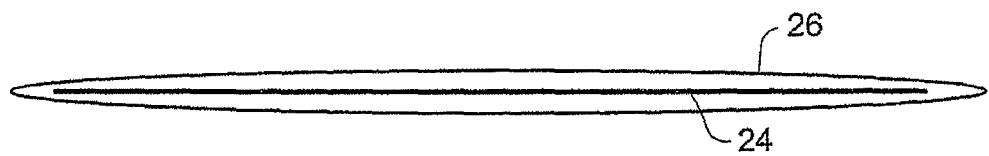
FIGS. 4A and 4B schematically depict a heating element according to a sample embodiment of the invention.
Figure 4B:
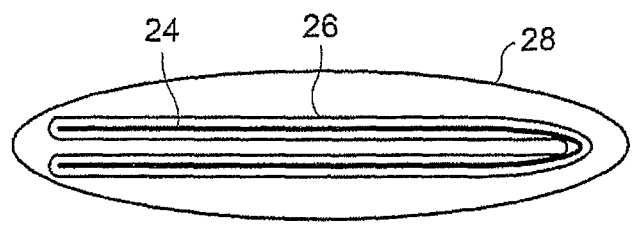

Referring to FIGS. 4A and 4B, in another sample embodiment of the heating element, a single resistive ribbon wire 24 is coated with an insulating layer 26 and the resulting structure is folded in half and then coated again in a second insulating layer or protective outer layer 28 to form the heating element 12.

Heating Element and Delivery Conduit

Figure 5:
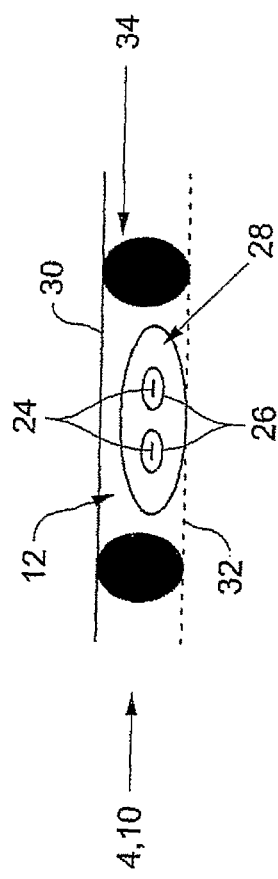
FIG. 5 schematically depicts a conduit including a heating element according to a sample embodiment of the invention.

As shown in FIG. 1 the heating element 12 may be incorporated within the inlet conduit 10 and/or the patient conduit 4. The heating element 12 may comprise different heating elements or zones. For example, as shown in FIG. 1, the heater element 12 may comprise a first heater element or zone 18 located in the inlet conduit 10, a second heater element or zone 16 located within the humidifier chamber 1, and a third heater element or zone 19 located in the patient conduit 4. Connectors 2, 11 provide the power and communication signals to each of the different heating elements or zones. Each heating element or zone 18, 16, 19 may be independently controlled to provide the required temperature and humidity conditions required. As shown in FIG. 5, the conduit 4, 10 may be formed by an inner layer 32 and an outer layer 30 which is supported on the inner layer by supports 34. The inner layer 32 may be formed of a semi-permeable membrane, or of a membrane having small perforations formed therein. The heating element 12 is wound around the inner layer 32 of the conduit 4, 10 between the supports 34. The upper layer 30 is then wound around the supports 34 and the heating element 12 to provide a twin walled conduit.

As shown in FIGS. 2-5, the resistive wires are shown and described as ribbons. However, it should be appreciated that round wires may also be provided to form the heating element 12. It should also be appreciated that the heating element 12 may be any of the heating elements as shown in FIGS. 2-4B.

The resistive ribbon wires 24, 24a, 24b may be formed, for example, of a nickel chrome alloy, such as NIKROTHAL® from Kanthal. Other suitable resistive ribbon wires may be used and formed from, for example, copper, silver and/or other metals. The thickness of the resistive ribbon wires 24, 24a, 24b may be $\frac{1}{16}$-$\frac{3}{16}$ of an inch, for example $\frac{1}{8}$ of an inch. It should be appreciated, however, that other thicknesses may be used.

The insulating layers 26, 26a, 26b may be formed, for example, of KAPTON® or polyester or polyimide. The insulating layer 26, 26a, 26b may be adhesively attached to at least one surface of the resistive ribbon wire 24, 24a, 24b. Alternatively, the insulating layer 26, 26a, 26b and/or a protective outer layer 28 may be heat-shrunk onto the resistive ribbon wire. The resistive ribbon wire(s) may also be coated with a dipped insulating layer 26, 26a, 26b and/or protective outer layer 28.

Referring again to FIG. 1, the heating element 12 may be used to heat the flow of breathable gas, the water, and/or any other fluids. As shown in FIG. 1, the heating element 12 heats the flow as it enters the humidifier chamber 1 and then heats the water 13 and continues through the patient conduit 4 to provide heat to the flow of gas and water vapor in the patient conduit 4. The heating element 12 may be insulated within conduit(s) 4, 10 and inserted into the conduit(s) 4, 10 as it provides minimal impedance. Alternatively, the heating strip may be welded into the conduit(s) 4, 10 so as to be held in one position within the conduit(s) 4, 10 as opposed to free in the conduit(s) 4, 10. According to another sample embodiment of the invention, the heating element 12 may be provided within the conduit(s) 4, 10 in a second, smaller conduit(s) used to hold the heating element 12.

The heating element 12 according to the sample embodiments discussed above provides almost instant heat delivery to the flow of pressurized gas. By providing the heating element 12 from the flow generator 22 to the humidifier chamber 1, the heated flow of breathable gas vaporizes more of the water 13 and provides a higher level of humidity to the patient interface 5. By providing the heating element 12 in the patient conduit 4, rain out in the patient conduit is prevented as the flow of breathable gas is delivered to the patient interface 5 without condensation in the conduit 4.

The heating element 12 is also low cost to manufacture. By providing the heating element 12 from the flow generator to the patient interface, no separate heating elements are required as the heating element 12 is one continuous strip that may be located where the heating is required. The heating efficiency of the respiratory apparatus is thereby increased.

The heating element 12 also reduces the risk of water leakage as no seals are required in the humidifier chamber below the surface 14 of the water 13. The heating element 12 also provides independent heating and humidification with respect to a humidifier which may be incorporated with the flow generator.

The heating element 12 also allows the system to be portable and has low power requirements. The heating element 12 is also easily replaceable within the respiratory apparatus.

Heating Element and Wicking Element

Figure 6:
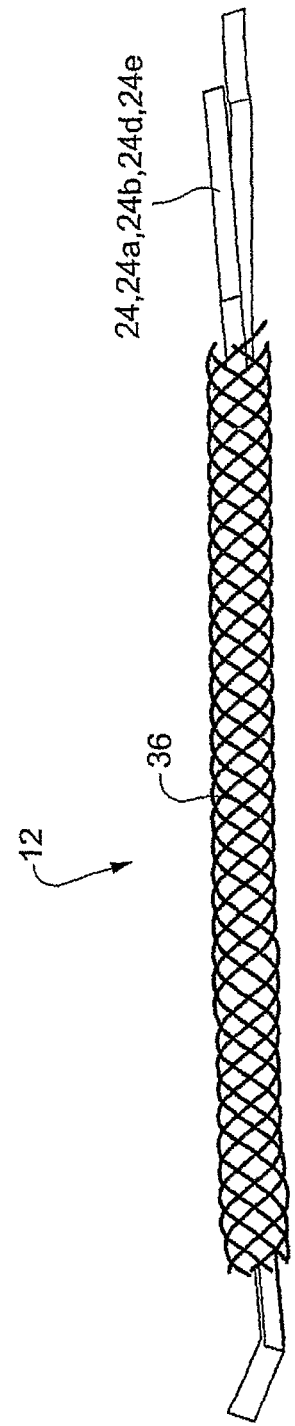
FIG. 6 depicts a heating element including a wicking element according to a sample embodiment of the invention.
Figure 7:
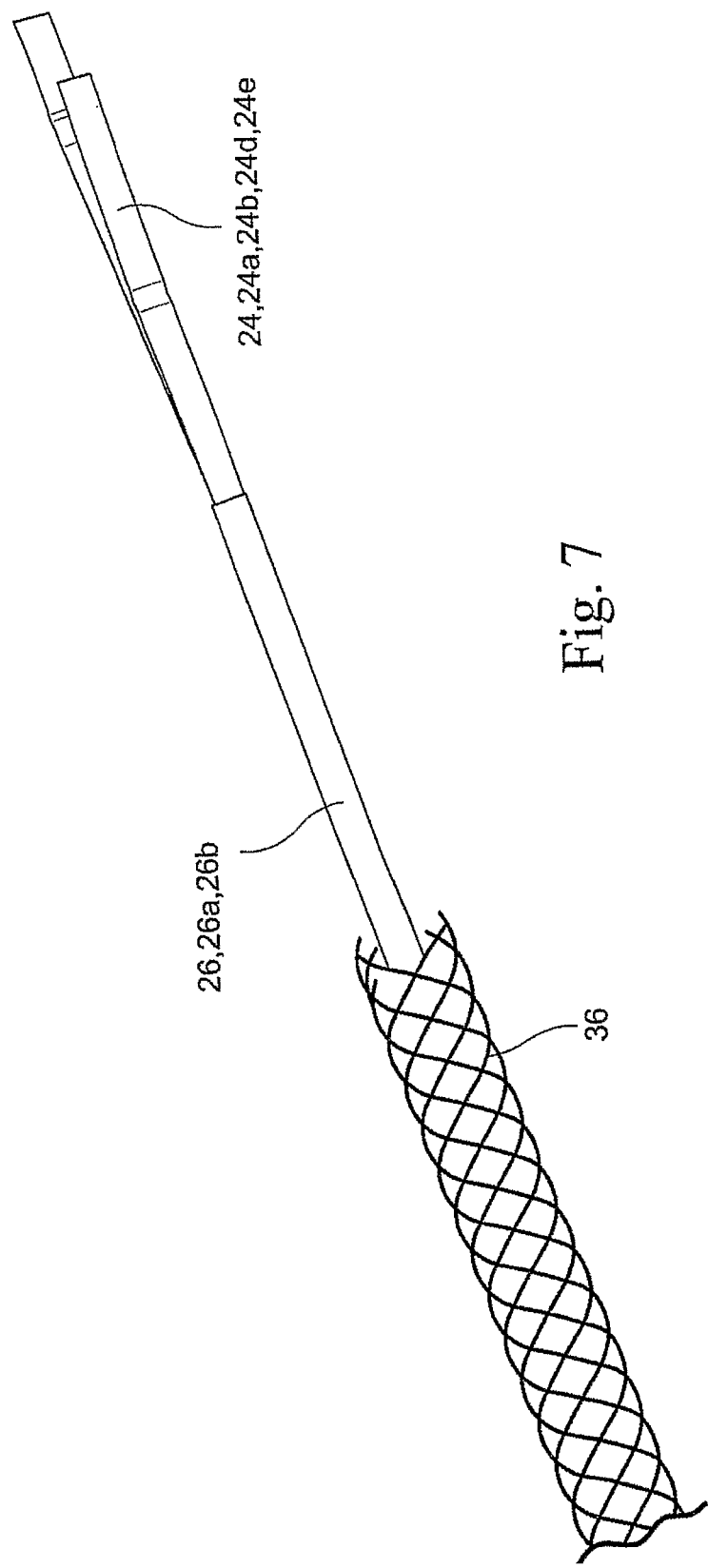
FIG. 7 depicts a heating element including a wicking element according to a sample embodiment of the invention.

Referring to FIG. 6, the heating element 12 may be provided with a wicking element 36 around the resistive ribbon wires 24, 24a, 24b, 24d, 24e, which may optionally be covered with an insulating layer and/or a protective outer layer. The wicking element 36 may be formed, for example, of woven cotton in a tubing shape, e.g. similar to shoelaces. The wicking element may be provided along the entire length of the heating element 12, or may be provided only in certain portions of the respiratory apparatus. For example, the wicking element 36 may be provided to the heating element 12 only in the humidifier chamber 1. As another example, the wicking element 36 may be provided to the heating element 12 in the patient conduit 4. The wicking element increases the amount of water vapor that may be provided into the patient conduit 4. As the wicking element is provided as a further layer over the heating element 12, the wicking element in combination with the heating element 12 acts as a powered wick.

As shown in FIG. 7, the wicking element 36 may be provided to less than the entire length of the heating element. Portions of the insulating layer 26, 26a, 26b, and/or the protective outer layer 28, may not be covered by the wicking element 36 so that portions of the heating element are exposed directly to the flow of breathable gas.

It should also be appreciated that the wicking element may be provided without a heating element. The wicking element may be provided in the inlet conduit 10, the humidifier chamber 1 and/or the patient conduit 4. The wicking element holds water so as to be in contact with the flow of breathable gas.

Humidifier with Heating Element

Figure 8A:
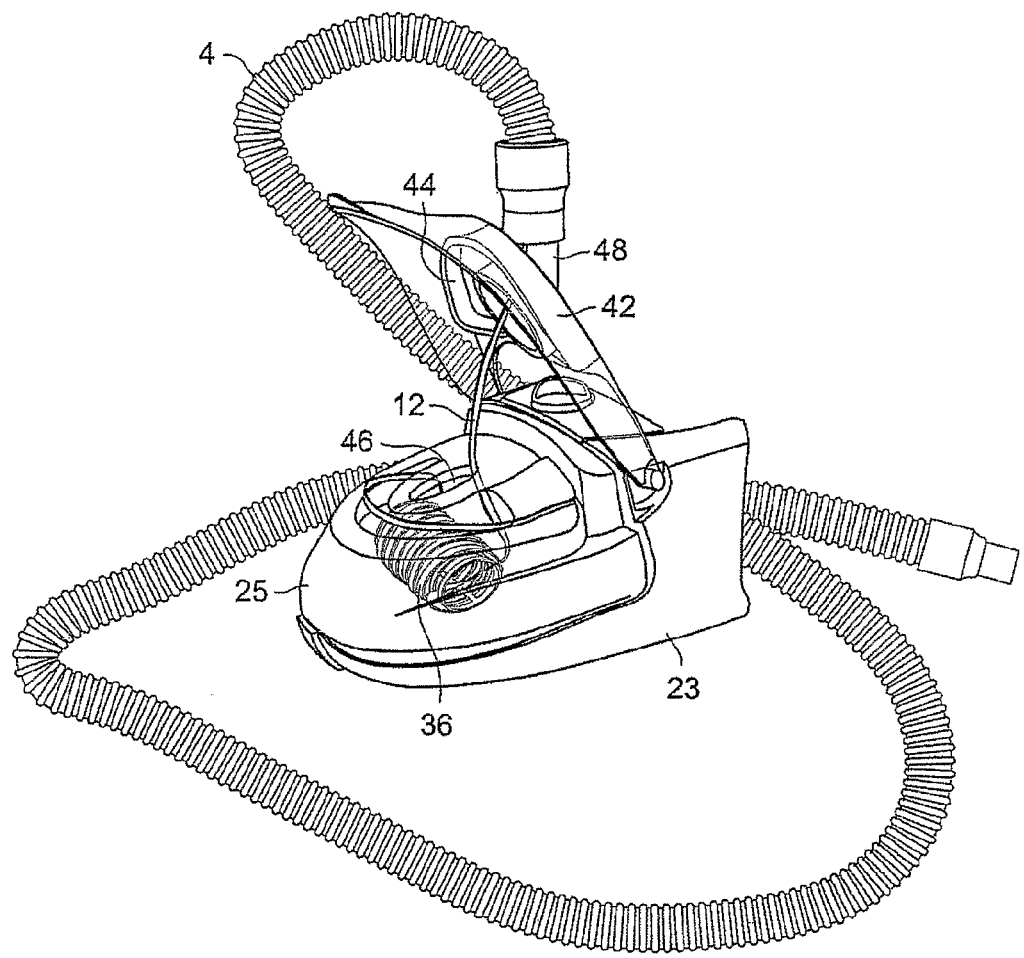
FIGS. 8A and 8B depict a humidifier including a heating element according to a sample embodiment of the invention.
Figure 8B:
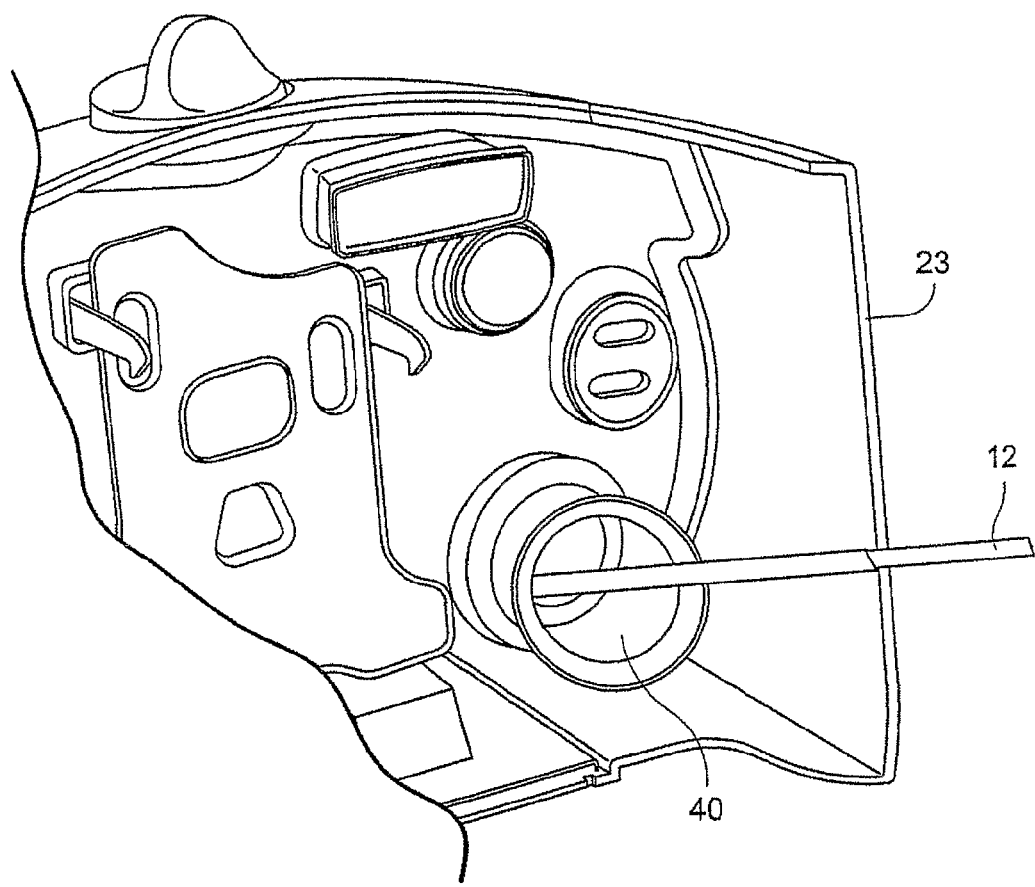

Referring to FIGS. 8A and 8B, a humidifier 23 may be provided with a heating element 12 according to a sample embodiment of the invention. The humidifier may be one as disclosed in co-pending, commonly assigned U.S. Patent Application Publication 2008/0072900 A1, the entire contents of which are incorporated herein by reference. The humidifier 23 may be connected to the flow generator 22 to present an integrated unit. The heating element 12 is connected to the power supply and controller 21 and threaded through the flow generator 20 into the humidifier 23. The humidifier 23 includes a tub 25 which is configured to hold a supply of water. A heating element in form of a plate (not shown) may be provided in the humidifier 23 to heat the water in the tub 25.

The humidifier 23 comprises an inlet 40 to receive the flow of breathable gas from the flow generator. A hinged lid 42 is connected to the humidifier 23 to cover the tub 25. The lid 42 may include a seal 44 to provide a vapor tight connection with an outlet 46 of the tub 25. The lid 42 of the humidifier 23 may include an outlet 48 for connection of the patient conduit 4. The heating element extends from the inlet 40, through the tub 25 and the outlets 46, 48 into the patient conduit.

Humidifier with Heating Element and Wicking Element

Figure 9:
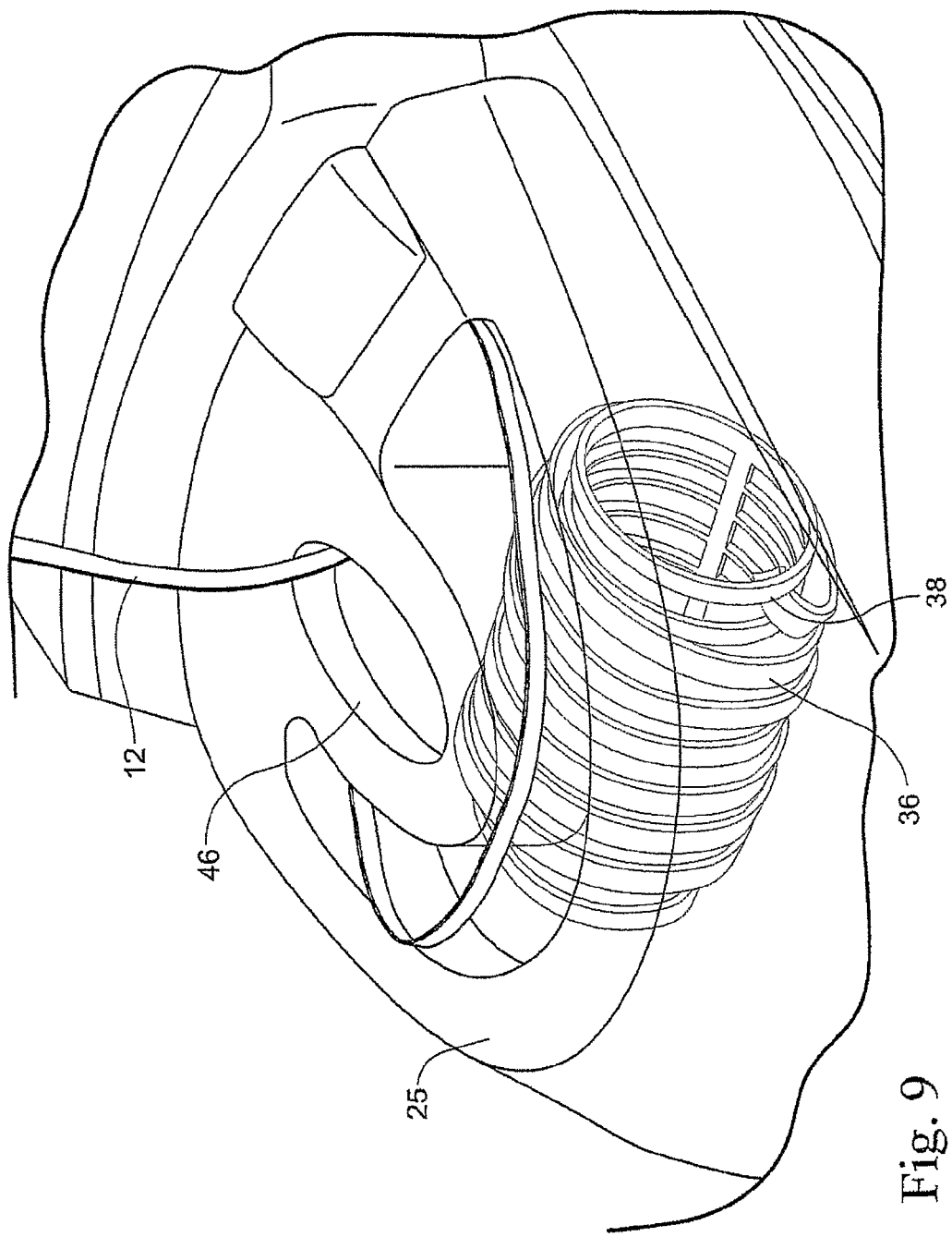
FIG. 9 is an enlarged view of the humidifier of FIG. 8.

The heating element 12 is provided in the tub 25 and the portion of the heating element 12 in the tub 25 has wicking element 36 provided around the protective outer layer 28. The portion of the heating element 12 provided with the wicking element 36 is supported by a wicking support 38. As shown in FIGS. 8A, 8B and 9, the wicking support 38 is a tubular structure around which the heating element 12 and wicking element 36 are wound. As also shown in FIG. 9, the wicking element 36 is provided on the heating element 12 only on the portions supported by the wicking support 38, but it should be appreciated that the wicking element 36 may be provided to any portion(s) of the heating element 12, or to the entire heating element 12.

Wick Absorbing Condensation

The wicking element may also be used to absorb any condensed water present in the respiratory apparatus. For example, water that is condensed in the patient conduit 4 may be absorbed by wicking element 36 present in the patient conduit 4. The condensed water absorbed by the wicking element 36 may be re-evaporated to provide additional humidity to the air flowing in the system. In one embodiment, the heating element 12 may comprise sections covered with the wicking element 36 that are not provided water from a water reservoir but simply absorb condensing water present in the humid environment. For example, referring to FIG. 1 the heating element or zone 19 may be covered with wicking element 36 and heating elements or zones 16, 18 may not be covered with wicking element 36 but simply heat the water and/or air. In this embodiment the wicking element does not receive water directly from a water reservoir or the humidifier tub. Any water that is condensed in the patient conduit 4 is absorbed by the wicking element 36. Advantageously, in this manner the water absorbed by the wicking element is pure water as any impurities, such as minerals, present in the water will remain in the water tub rather than be evaporated into the air flow. Thus the wicking element remains clean from impurities such as mineral deposits.

Humidifier Chamber with Wicking Element

Figure 10:
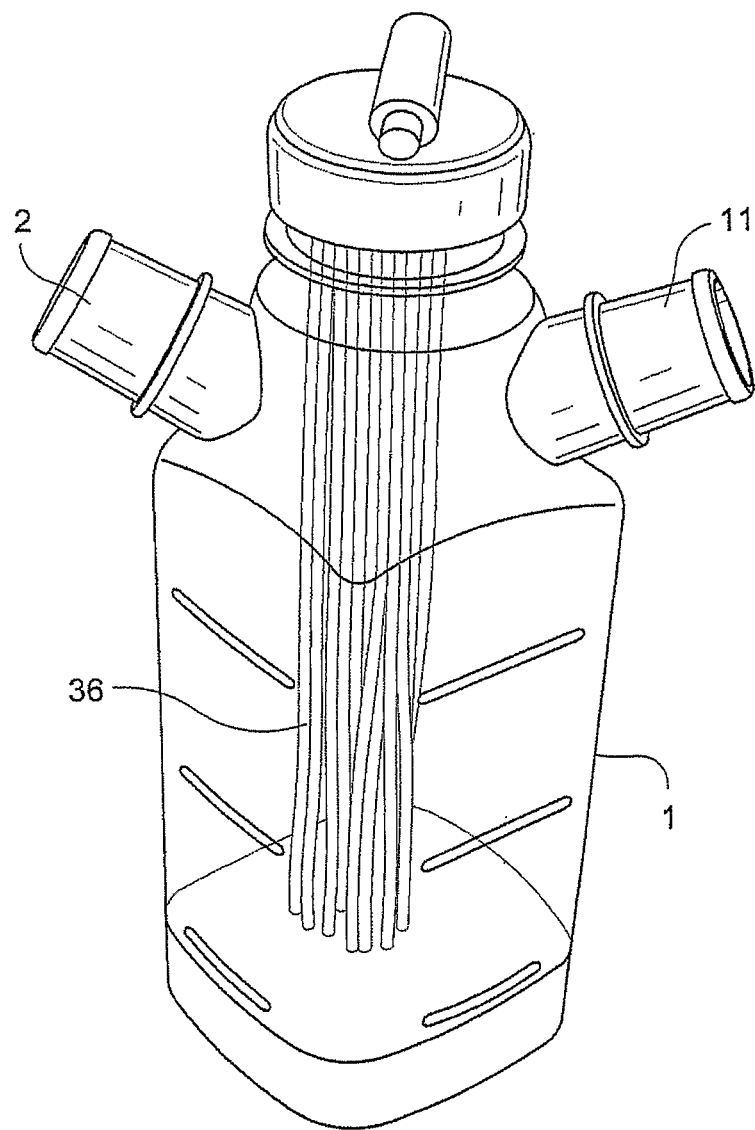
FIG. 10 depicts a humidifier chamber including a wicking element according to a sample embodiment of the invention.

Referring to FIG. 10, the humidifier chamber 1 may also be provided with wicking element 36 to increase the surface area in contact with the flow of breathable gas. As the flow of breathable gas passes the wicking element, the water held by the wicking element 36 is vaporized and carried through the outlet 2 of the humidifier chamber 1 into the patient conduit 4.

Humidifier Chamber with Heating Element and Wicking Element

Figure 11:
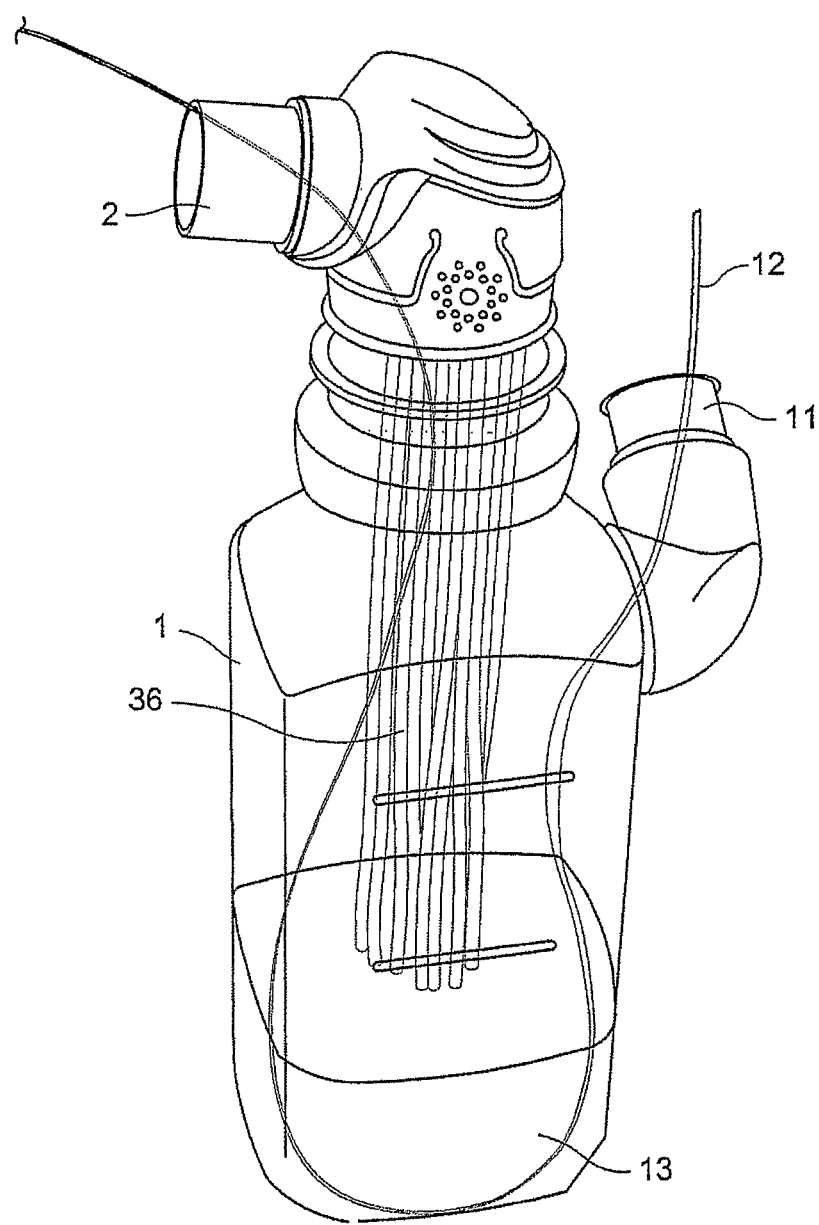
FIG. 11 depicts a humidifier chamber including a wicking element and a heating element according to a sample embodiment of the invention.
Figure 12:
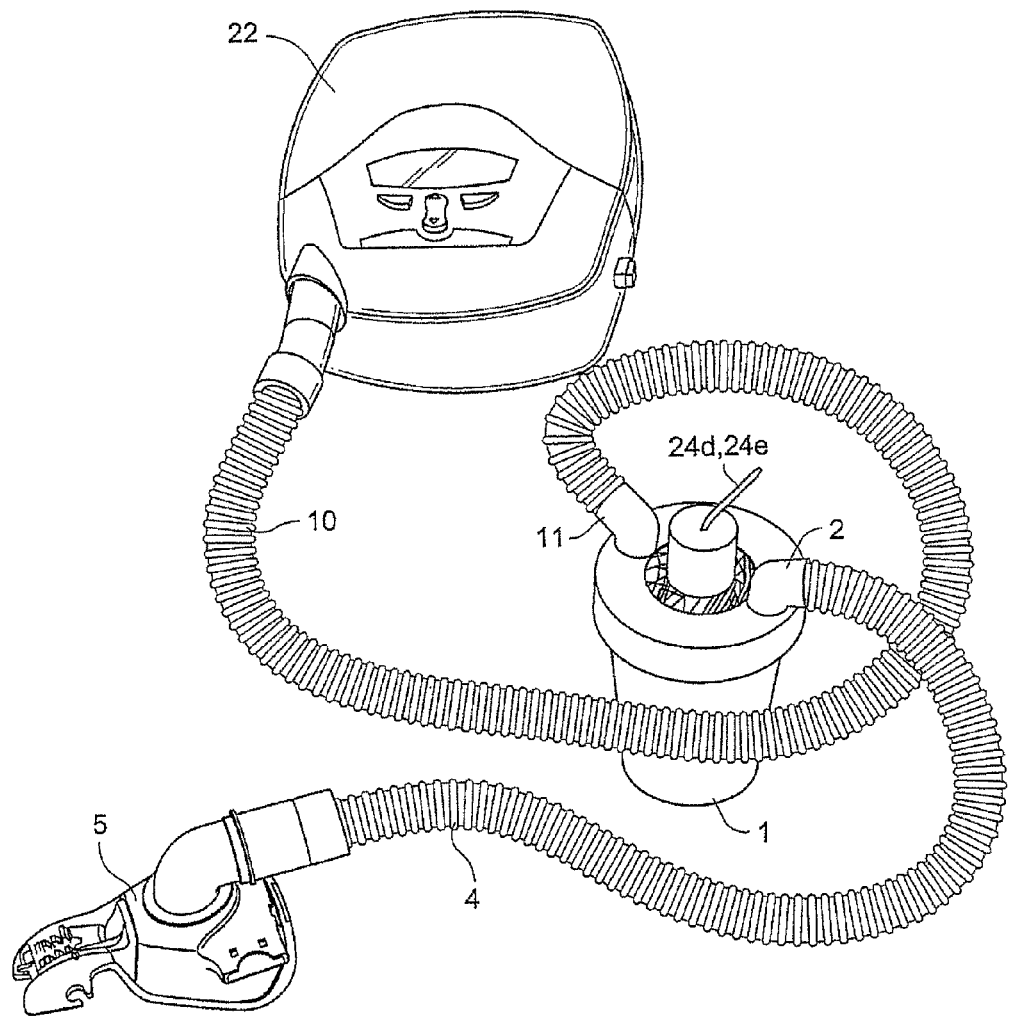
FIG. 12 depicts a respiratory apparatus including a humidifier chamber including a heating element, a wicking element and a wicking element support according to a sample embodiment of the invention.
Figure 13:
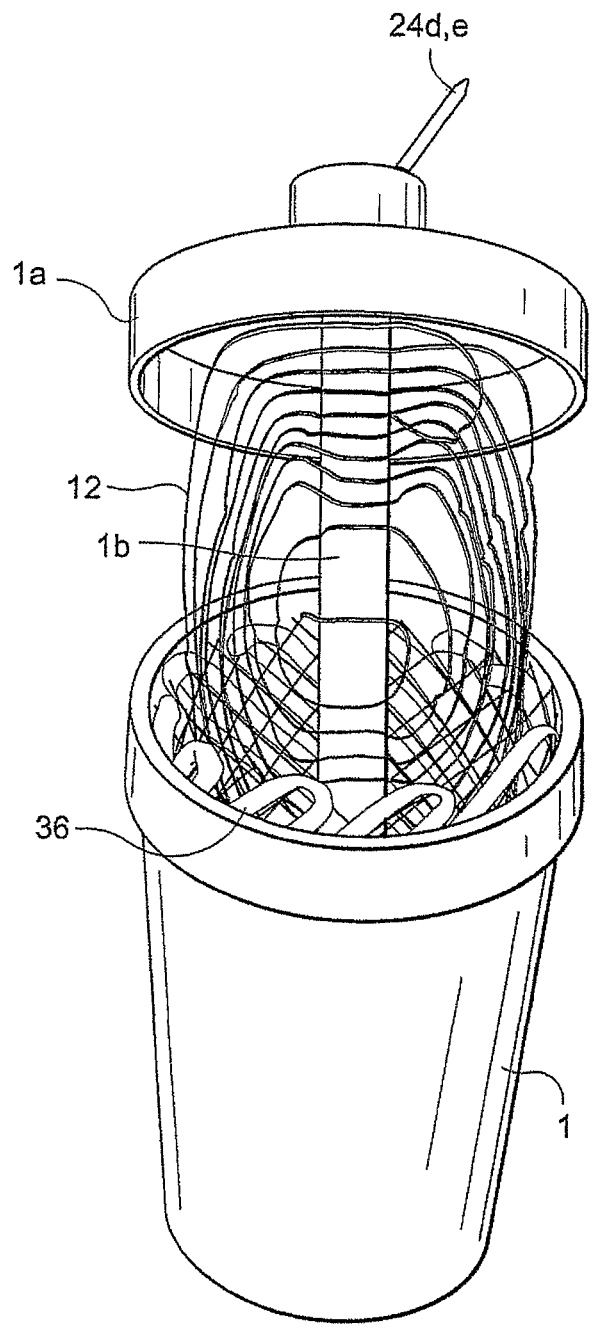
FIG. 13 depicts the humidifier chamber, the heating element, the wicking element and the wicking element support of FIG. 12.

As shown in FIG. 11, the humidifier chamber 1 may also be provided with a heating element 12 in addition to the wicking element 36. By providing the wicking element 36 and the heating element 12 separately, the heat and humidity of the flow of breathable gas may be adjusted independently. The amount and the pattern of the wicking element may be varied to provide different levels of humidity. A single wicking element may have a high amount of wick on one surface and less, or no, wicking on another surface. By twisting or rotating the support of the wicking element to direct the different surfaces in the main path of the flow of breathable gas, a different level of humidity may be provided.

Humidifier Chamber with Heating Element and Wicking Element Support

Figure 14:
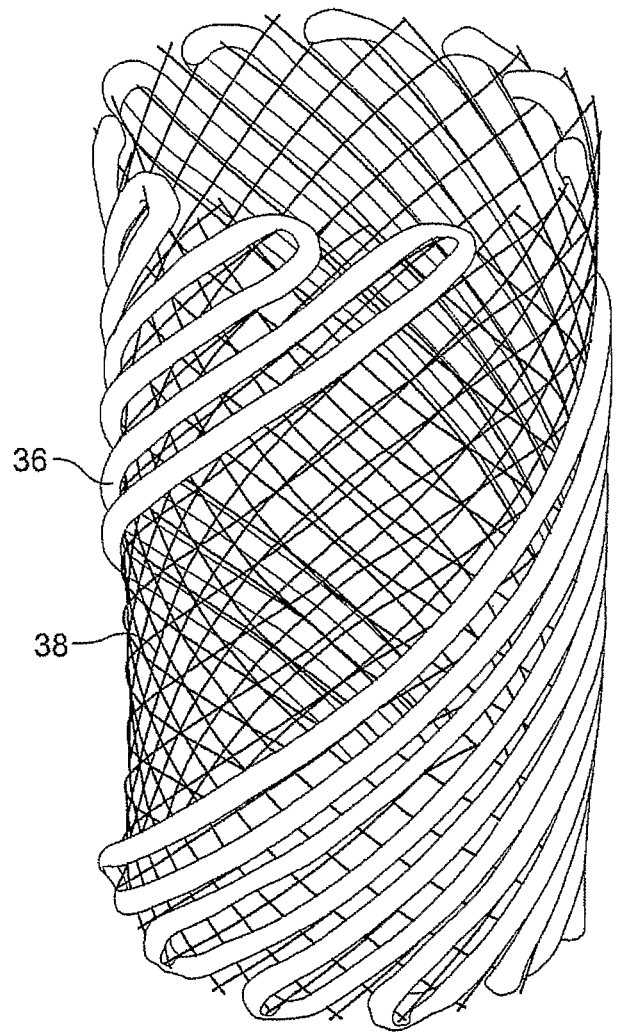
FIG. 14 depicts the wicking element and the wicking element support shown in FIG. 13.
Figure 15:
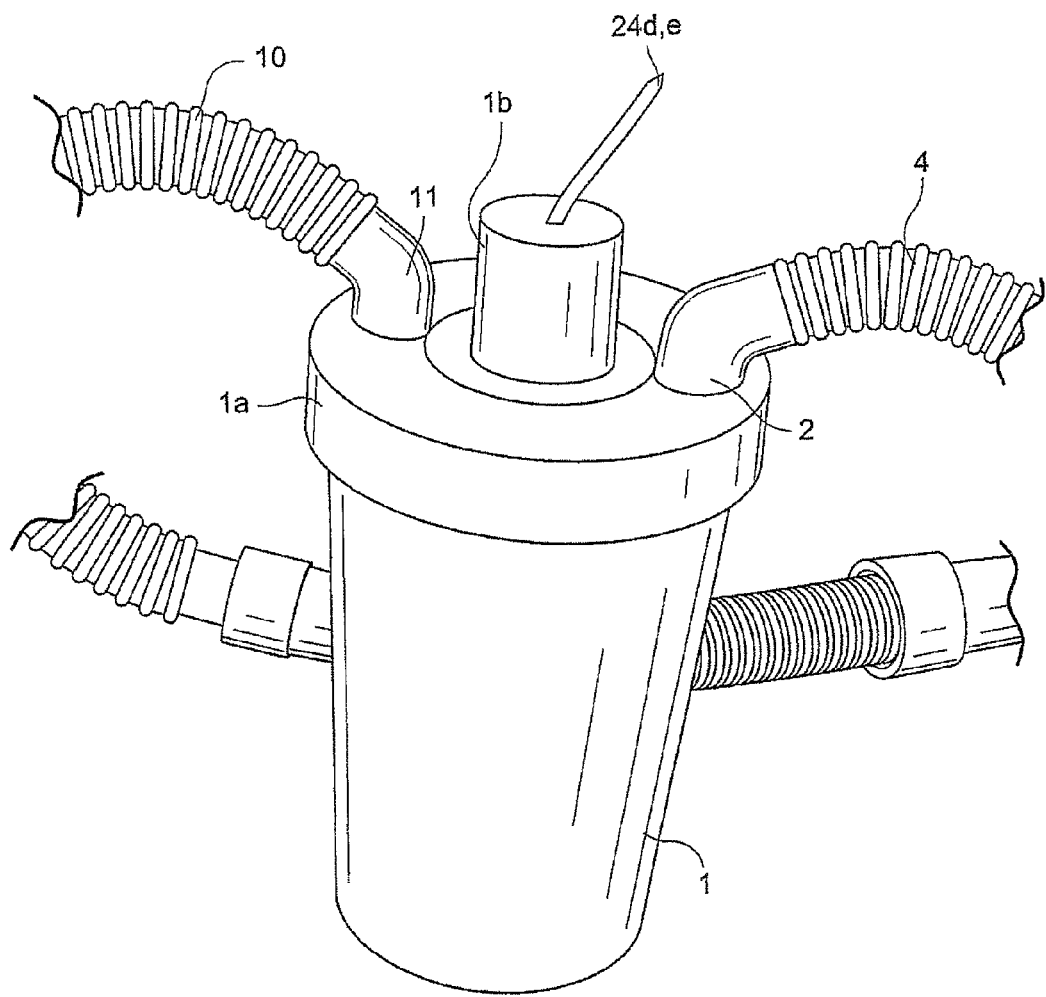
FIG. 15 depicts the humidifier chamber of FIGS. 12-14.

Referring to FIGS. 12-15, the humidifier chamber 1 may be provided with a heating element 12 in the form of a spiral. It should be appreciated that the heating element may be formed into other shapes, such as a helix or in a tubular configuration as shown in FIG. 9. Forming the heating element as a spiral or helix or in a tubular configuration increases the amount of water and flow of breathable gas in contact with the heating element, thereby allowing increased humidification at a lower power supply to the heating element, and finer control of the amount of humidification. The heating element 12 may be supported by a post 1b which is connected to a cover 1a of the humidifier chamber 1. The ends 24d, 24e of the resistive ribbon wires of the heating element 12 may extend through the top of the post 1b for connection to the flow generator 22 or the power supply and controller 21. As shown in FIG. 14, the wicking element 36 is supported by the wicking support 38, which may be in the form of a tubular mesh structure.

Variable Wicking Element Support

Figure 16:
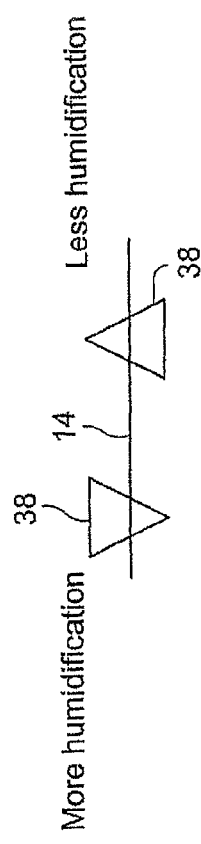
FIG. 16 schematically depicts two configurations of a wicking element support according to sample embodiments of the invention.

Referring to FIG. 16, the wicking support 38 may have a pattern and/or a shape to assist in controlling the level of heating and humidification required. For example, the wicking support 38 may be triangular in shape and provided on the surface 14 of the water 13 of the humidifier chamber 1 so that a majority of the wicking support 38 is provided above the surface 14 of the water 13. This provides a larger amount of humidification of the flow of breathable gas. Conversely, the wicking support 38 may be provided so that a majority of the wicking support 38 is provided below the surface 14 of the water 13 to provide less humidification to the flow of breathable gas. It should be appreciated that the wicking support 38 may take any one of an infinite number of positions between those shown in FIG. 16 to provide continuous control of the humidification of the flow of breathable gas. Although the wicking support 38 shown in FIG. 16 is depicted as triangular, it should be appreciated that other shapes may be provided. For example, the wicking support 38 may be trapezoidal, or generally trapezoidal.

Flat Wire Heating Element

In the sample embodiments discussed above, the heating element 12 may include a flat wire. The use of a flat wire provides advantages over round wires because it presents a larger surface area to the flow of gas and/or the water in the humidifier chamber than a round wire. The increased surface area also provides better mixing than a round wire as it forces the flow of breathable gas passing over the flat wire into a helical flow pattern. The mixing of the flow of breathable gas and water vapor provides a more uniform temperature distribution throughout the flow. However, it should be appreciated that the flat wire may not be made too large (e.g. too wide) as it may obstruct the flow of breathable gas too much. The use of a flat wire also prevents the heating element from heating the tube to an unsafe temperature as only the edges of the flat wire contact the tube.

A flat wire also has less impedance than a round wire. A heating element formed of a flat wire is thus more responsive to a voltage change than a heating element formed of a round wire. The humidity of the flow of breathable gas may therefore be controlled by controlling the voltage applied to the flat wire. As a flat wire has less impedance, the power requirements for the heating element are reduced. The size of a power pack configured to deliver current to the heating element may thus be reduced, or batteries may be used to deliver current to the heating element. Due to the reduced impedance, a flat wire also takes less time to warm up than a round wire for the same amount of power. For example, a flat wire may achieve a desired temperature in seconds, as opposed to minutes for a round wire, given the same amount of power. The ability to achieve a desired temperature using less power (e.g. voltage) and/or in a shorter time period than a round wire makes use of a flat wire more efficient than a round wire.

The choice of material may determine the maximum power (e.g. voltage) that may be applied to the flat wire and the maximum temperature to which the flat wire may be heated. As discussed above, the flat wire may be made, for example, of a nickel chrome alloy, a nickel chrome iron alloy, copper, silver, and/or other metals. In the case where the flat wire is formed of an alloy, e.g. nickel chrome, the percentages of each metal in the alloy may be selected to control the maximum power and temperature of the flat wire.

The flat wire may also be formed of a Positive Temperature Coefficient (PTC) material. A PTC material is one in which the resistance of the material increases with increasing temperature, for example an increasing temperature resulting from application of a constant voltage. As the resistance of the material increases, the current provided by the constant voltage decreases. The PTC material thus provides a self limiting effect on the material of the flat wire. The PTC material may be selected so that the flat wire may only attain a maximum temperature, for example 70° C.

The use of a PTC material for the flat wire also allows the measurement of the temperature of the wire. As the temperature of the flat wire is directly proportional to the voltage that is applied to the flat wire, the application of a known voltage will result in a known temperature.

As discussed above, the heating element 12 may be provided in any portion of the respiratory apparatus, including in the humidifier (e.g. separate or integrated with the flow generator, ore merely including a humidifier chamber to contain water), the inlet conduit, and/or the patient conduit. As also discussed above, wicking element may be provided to the heating element 12. The wicking element may be provided to the heating element in the humidifier, the inlet conduit, and/or the patient conduit. A wicking element provided on the flat wire may act as an insulator and allow more accurate control of the heat provided by the flat wire.

The use of a wicking element may allow the control of the temperature and humidity throughout the components of the respiratory apparatus. As the temperature and humidity of the breathable gas in the humidifier chamber may be more easily determined and controlled, as the humidifier chamber represents a rather small space as opposed to a conduit that may be, for example, 1 m or longer, the temperature and humidity in the humidifier chamber may be used to control the temperature and humidity in the inlet conduit and/or the patient conduit. As the voltage applied to the flat wire corresponds to the temperature of the flat wire, the voltage may be selected and applied to the flat wire in the inlet and/or patient conduit so that the temperature and humidity in the conduit(s) corresponds to the temperature and humidity in the humidifier chamber so as to prevent rain out in the conduit(s). This configuration also makes it unnecessary to provide temperature sensors in the conduit(s).

Changing the voltage applied to the flat wire produces a corresponding change in temperature, and therefore a corresponding change in the humidity. In the case where no wicking element is provided on the flat wire, the change in voltage will produce almost instantaneous changes in temperature and humidity. If a wicking element is provided to the flat wire, the wicking element acts as an insulator and produces a delay in the change of temperature and humidity after a change in applied voltage. However, as the wicking element on the flat wire in a conduit(s) holds water, the temperature and humidity in the conduit(s) may be controlled. A change in the applied voltage that results in a humidity exceeding 50% is significant.

The flat wire may be integrated into the tube, for example by routing the flat wire through an existing connector configured to connect the conduit to the flow generator, humidifier, and/or patient interface. As another example, a cuff, such as that disclosed in U.S. Patent Application Publication 2008/0105257 A1, which is incorporated herein by reference, may be co-molded to the conduit(s). The cuff may include electrical elements, e.g. a circuit or terminal(s) or electrical contact(s), to which the flat wire may be connected.

Heating Element Fourth Embodiment

Figure 17:
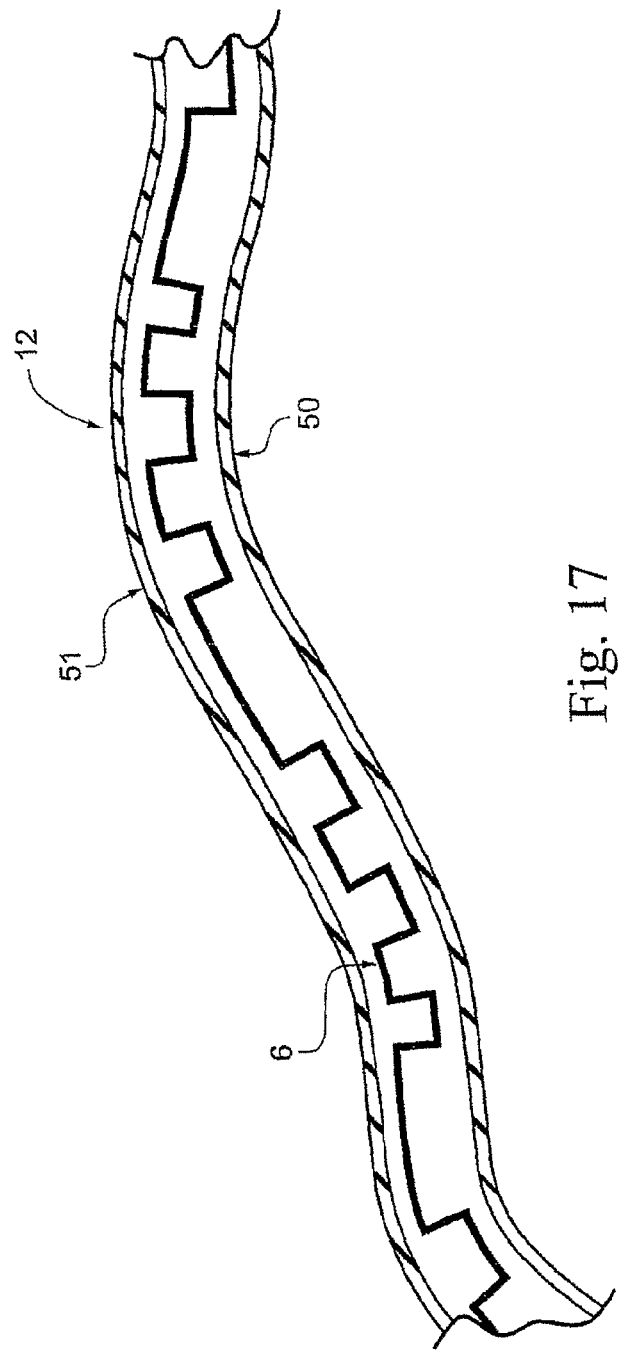
FIG. 17 schematically depicts a heating element according to a sample embodiment of the invention.

Referring to FIG. 17, the heating element 12 may also take the form of a ribbon. The ribbon may include a circuit 6 that is formed by printed circuit techniques applied to a surface of a flexible substrate 50, such as KAPTON®, silicone rubber, all-polyimide, and PTFE. Printed circuit techniques which may be used include, for example, etched foil, vacuum deposition techniques, and printing techniques. For example, the circuit 6 may be formed by conductive inks, e.g. carbon and/or silver, printed on the substrate 50. The substrate 50 may comprise, for example, a polymer thin film.

Another substrate 51 may then be laid upon the substrate 50 and the circuit 6 and the two substrates 50, 51 may be adhered or fused together to encapsulate the circuit 6. The Thermofoil™ range of the type of flexible heaters by Minco of Minneapolis USA, described at www.minco.com, are examples of commercially available strip heaters which may be used in the present invention.

An alternative embodiment to produce the heating element 12 may use a laminator, such as a twin silicon roller laminator, to encapsulate the circuit 6, which may be in the form of wire or ribbon, within two substrates of polycarbonate film. The resulting heating element 12 may, for example, have dimensions ranging from about 1-10 mm wide, for example about 5 mm wide, and about 0.1-1 mm thick, for example about 0.2-0.5 mm thick. A heating element having dimensions in these ranges may be used in the inlet conduit 10 and the patient conduit 4.

The heating element 12 may have any suitable transverse cross-section, for example circular, elongate or rectangular. For example, the heating element 12 may be flat in a manner similar to the flat wire heating element discussed above. The circuit 6 may, for example, comprise a resistive conductor.

The arrangement of the circuit 6 between the laminating films may be any ordered or disordered arrangement that increases the heat transfer of the heating element 12 to the surrounding media, be it gas or liquid. The circuit 6 may also have a positive thermal coefficient (PTC) for resistance such that heating decreases as the temperature increases towards a desired temperature.

Alternatively the circuit 6 may have a negative thermal coefficient (NTC) to allow sensing of the temperature of the circuit 6 or surrounding media.

In another embodiment, there may be multiple circuits within the heating element 12. The multiple circuits may be connected in series and/or parallel. The use of these multiple circuits within a heating element 12 enables additional heating to be applied as required in the operation of the respiratory apparatus.

In a further embodiment, the substrates may be polyester, polypropylene or any suitable and approved substance for respiratory medicine use. Alternatively, multiple laminating substrates may be used to create a composite strip having the desired properties while retaining the desired compatibility of the outer film for respiratory medicine use. Other conductors may also be present between each of these multiple layers, for example so as to form multiple circuits, such as to allow multiple heating zones along the length of the tape heater.

Heating Element Fifth Embodiment

Figure 18A:
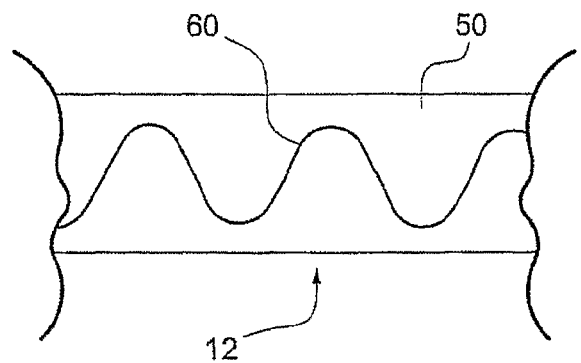
FIGS. 18A-18C schematically depict a heating element according to sample embodiments of the invention, wherein FIG. 18A schematically illustrates a plan view of a portion of a heating element according to a sample embodiment, FIG. 18B schematically illustrates a plan view of a portion of a heating element according to a sample embodiment.
Figure 18B:
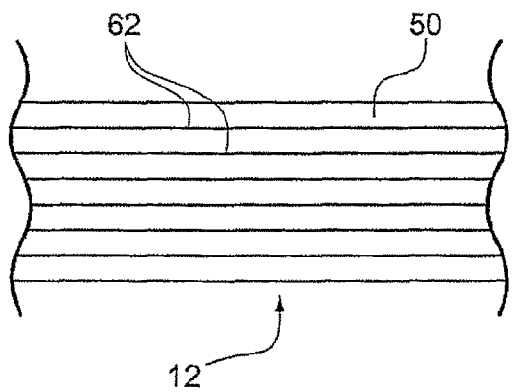
Figure 18C:
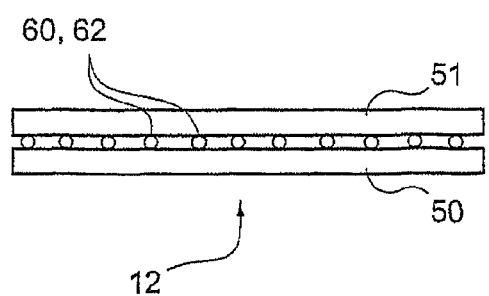

Referring to FIG. 18A, heating element 12 includes a substrate 50 in the form of a ribbon. A wire 60 is placed on the substrate 50. The wire 60 may be placed on the substrate in a serpentine fashion. It should be appreciated, however, that other patterns of placing the wire 60 on the substrate 50 may be used, or that multiple wires 62 may be placed on the substrate 50, for example in parallel, as shown in FIG. 18B.

The heating element 12 may include a second substrate 51 to encapsulate the wire(s) 60, 62. The substrates 50, 51 may be insulating films, such as polymer thin films.

Heating Element Sixth Embodiment

Figure 19:
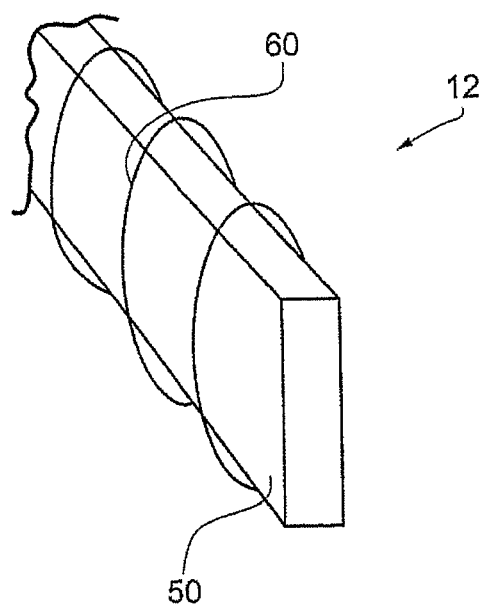
FIG. 19 schematically depicts a heating element according to a sample embodiment of the invention.

Referring to FIG. 19, the heating element 12 may be a substrate 50 in the form of a ribbon. A wire 60 may be wrapped around the substrate 50. The substrate 50 may be formed from an insulative film, such as a polymer thin film.

Heating Element Seventh Embodiment

The inlet conduit 10 and/or the patient conduit 4 may have electrically conductive ink 70 printed directly on the outer surface. The electrically conductive ink may be carbon ink or silver ink or any other suitably electrically conductive ink. In a sample embodiment, the electrically conductive ink is printed on to the conduit(s) 4, 10 using a screen printing process. However, it should be appreciated that other printing processes may be used, for example etching. Processes for applying electrically conductive ink are disclosed in International Application PCT/AU2008/000799, filed Jun. 3, 2008, the entire contents of which are incorporated herein by reference.

Figure 20:
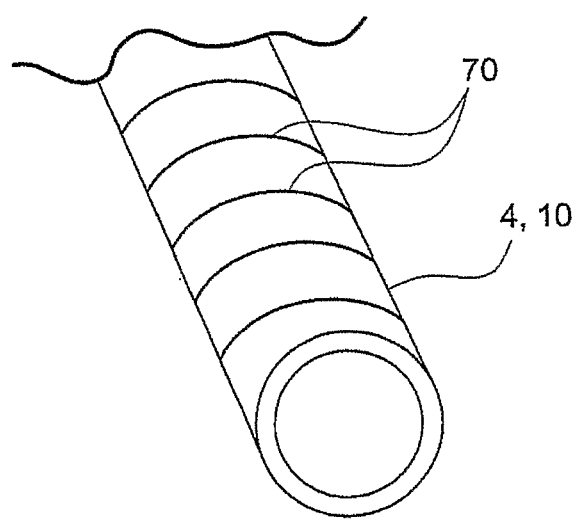
FIG. 20 schematically depicts a heating element according to a sample embodiment of the invention.

The pattern of the printed ink affects the distribution of the heat and the resistance. The pattern of the electrically conductive ink applied to the conduit(s) 4, 10 may be adjusted to provide different watt densities. The thickness, width and length and material properties (resistivity/conductivity) of the electrically conductive ink printed pattern determines the resistance. A thicker or wider ink pattern has lower resistance than thinner or narrow ink patterns, whereas the resistance increases with increasing lengths of the printed ink pattern. In a sample embodiment, the ink pattern may be designed to provide a given resistance to allow a particular voltage to be applied. For example, as shown in FIG. 20, the electrically conductive ink is provided in a helical pattern, for example to provide a uniform heating to the conduit(s) 4, 10. It should be appreciated that other patterns, e.g. serpentine, axial, etc., may be used to produce other heating effects to the conduit(s) 4, 10.

Furthermore, the conductive ink circuits may include a combination of conductive inks such as carbon and silver ink to provide different resistance properties within the heating element. Carbon ink has a much higher resistance compared to silver ink and may be used where heat generation is most important. For example, carbon ink may be printed on the conduit(s) 4, at a position farthest from the humidifier chamber to ensure that the temperature at the farthest position is adequate to prevent rain out. If the electrically conductive ink is a combination of silver and carbon inks, and/or other inks, the percentages of each electrically conductive ink in the mixture may be varied to produce a desired heating pattern.

It should be appreciated that although the electrically conductive ink is shown in FIG. 20 as being printed directly on the outer surface of the conduit(s) 4, 10, it is also possible to print the electrically conductive ink on the inner surface of the conduit(s) 4, 10, or in any combination of the inner and outer surfaces.

The heating elements disclosed herein may be used to control the temperature and humidity of a flow of breathable gas delivered to a patient without rain out of the water vapor in the tube(s) of the respiratory apparatus. The voltage applied to the heating element may be controlled to provide the desired temperature and humidity. For example, for respiratory apparatus being used in the home of the patient, the ambient temperature may range from about 5°-37° C. In a clinic or hospital setting, ambient temperature may range from about 25°-37° C.

Wicking Element

The wicking element may be formed of, for example, surgical cotton. In those embodiments in which the wicking element covers at least a portion of the heating element, the cotton, e.g. a thread, may be wound and/or fused onto the insulating layer of the heating element, for example in a helical fashion.

The wicking element may also be combined with the insulating layer(s) of the heating elements. The resistive ribbon wire(s) may be coated with a hygroscopic sponge material which is applied, for example, using a standard implantable type coating process. The hygroscopic sponge material may be applied during an inline, high speed integrated coating process using existing insulated wire technologies, which may reduce, or minimize, the cost of applying the wicking element.

For those embodiments in which the wicking element does not cover at least a portion of the heating element and for those embodiments which include a wicking element(s) without a heating element(s), the wicking element(s) may be formed of a hygroscopic sponge material or from a material woven of, for example, surgical cotton.

Cleaning and Disinfecting

To maintain clean breathable air, the system may be designed to perform a disinfection and/or cleaning wherein the heating element and the wicking element 36, if present, are heated to a sufficient temperature for a period of time to disinfect the air delivery conduits 4, and wicking element 36. The heating is sufficient to kill bacteria that may attempt to colonize in the damp humid conditions present in the respiratory apparatus and to dry the internal surface of the air delivery conduits. In the case where the wicking element is in contact with water in the humidifier chamber or tub, the wicking element may be disinfected, but not be completely "clean" as it may include impurities, such as minerals, that are present in the water from the humidifier chamber or tub. For example, if the wicking element is white, the wicking element may not appear "clean" (i.e. it may not be white) even after disinfection. In that instance, the wicking element may be further cleaned by, for example, rinsing the wicking element to remove impurities such as minerals and/or other particulate matter.

The heating may also dry the heating element covered with wicking element 36. For example, the heating element may heat the wicking element 36 to a temperature of about 45° C.-65° C. for approximately 5-60 minutes, for example about 5 minutes at about 60° C. or about 15 minutes at about 45° C. It should be appreciated that other temperatures and lengths of time may also be used. The respiratory apparatus may perform a self-disinfection that is activated before therapy commences or after therapy is completed or both before and after therapy or at some other programmed time. The self-disinfection may occur when the respiratory apparatus is not providing therapy.

The heating may be performed both prior to and after use of the humidifier for respiratory therapy. Heating prior to therapy may remove any residual water droplets from prior uses, which is beneficial as any water droplets from prior uses may rapidly increase in size from incoming humidity, which is detrimental to therapy. The heating may be performed after use to remove any water droplets that may have condensed, or "rained out" from the humidified air. Heating after use allows the humidifier and air delivery conduits to be stored dry, which may prevent growth of bacteria and/or viruses during periods of non-use.

While the invention has been described in connection with what are presently considered to be the most practical embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. Furthermore, each individual component of any given assembly, one or more portions of an individual component of any given assembly, and various combinations of components from one or more embodiments may include one or more ornamental design features. In addition, while the invention has particular application to patients who suffer from OSA, it is to be appreciated that patients who suffer from other illnesses (e.g., congestive heart failure, diabetes, morbid obesity, stroke, barriatric surgery, etc.) can derive benefit from the above teachings. Moreover, the above teachings have applicability with patients and non-patients alike in non-medical applications.

In this specification, the word "comprising" is to be understood in its "open" sense, that is, in the sense of "including", and thus not limited to its "closed" sense, that is the sense of "consisting only of." A corresponding meaning is to be attributed to the corresponding words "comprise, comprised and comprises where they appear.

It will further be understood that any reference herein to known prior art does not, unless the contrary indication appears, constitute an admission that such prior art is commonly known by those skilled in the art to which the invention relates.

The invention claimed is:

1. An apparatus for delivering breathable gas to a patient, comprising:
   a flow generator to generate a flow of breathable gas;
   a humidifier chamber to contain a supply of water;
   a first flow path to deliver the flow of breathable gas from the flow generator to the humidifier chamber;
   a second flow path to deliver the flow of breathable gas from the humidifier chamber to a patient interface; and
   a heating element extending through the first flow path, the humidifier chamber and into the second flow path.

2. An apparatus according to claim 1, wherein the heating element comprises:
   at least one resistive wire having a first end and a second end;
   an insulating layer between the first and second ends; and
   an outer coating surrounding the at least one resistive wire and the insulating layer.

3. An apparatus according to claim 2, wherein the at least one resistive wire comprises two resistive wires that are electrically connected.

4. An apparatus according to claim 2, wherein the at least one resistive wire comprises a ribbon wire.

5. An apparatus according to claim 1, further comprising a wicking element provided in at least one of the humidifier chamber and/or the second flow path.

6. An apparatus according to claim 1, wherein at least one of the first flow path and the second flow path comprises a conduit having an inner wall and an outer wall, and the heating element is provided between the inner wall and the outer wall.

7. An apparatus according to claim 6, wherein the inner wall is semi-permeable or perforated.

8. An apparatus according to claim 5, wherein the wicking element is provided in at least two of the first flow path, the second flow path, and the humidifier chamber.

9. An apparatus according to claim 8, wherein the wicking element is provided around at least a portion of the heating element.

10. An apparatus according to claim 5, wherein the wicking element absorbs condensed water within at least the second flow path.

11. An apparatus according to claim 5, wherein the wicking element comprises a woven material, a thread, or a hygroscopic sponge material.

12. An apparatus according to claim 5, further comprising a support in the humidifier chamber to support the wicking element.

13. An apparatus according to claim 12, wherein the support is a tubular support and the wicking element is provided on an outer surface of the tubular support.

14. An apparatus according to claim 13, wherein the heating element is provided around the tubular support.

15. An apparatus according to claim 13, wherein the heating element is provided inside the tubular support.

16. An apparatus according to claim 12, wherein the support is configured to selectively vary the amount of the wicking element exposed to the flow of breathable gas.

17. An apparatus according to claim 1, wherein the humidifier chamber comprises a tub of a humidifier, and the humidifier comprises a second heating element to heat the water supply.

18. An apparatus according to claim 1, further comprising a power supply and controller configured to supply and control power to the heating element.

19. An apparatus according to claim 18, wherein the heating element comprises a plurality of segments or zones.

20. An apparatus according to claim 19, wherein the power supply and controller is configured to supply and control power independently to each segment or zone.

21. An apparatus according to claim 18, wherein the power supply and controller is configured to supply power to the heating element prior to and/or after operation of the flow generator to generate the flow of breathable gas.

22. An apparatus according to claim 21, wherein the power supply and controller is configured to supply power to the heating element so that the heating element is heated to a temperature sufficient to kill bacteria and/or disinfect a wicking element provided in at least one of the humidifier chamber and/or the second flow path.

23. An apparatus according to claim 21, wherein the power supply and controller is configured to heat a wicking element provided in at least one of the humidifier chamber and/or the second flow path to a temperature of about 45°-65° C. for about 5-60 minutes.

24. An apparatus according to claim 23, wherein the power supply and controller is configured to heat the wicking element to about 60° C. for about 5 minutes.

25. An apparatus according to claim 23, wherein the power supply and controller is configured to heat the wicking element to about 45° C. for about 15 minutes.

26. A method of delivering a flow of breathable gas to a patient, comprising:
generating a flow of breathable gas; and
humidifying the flow by passing the flow over a supply of water, wherein humidifying the flow comprises heating the flow with a heating element in thermal contact with a) the flow before passing the supply of water, b) the supply of water, and/or c) the flow after passing the supply of water, the heating element extending from upstream of the supply of water to downstream of the supply of water.

27. A method according to claim 26, wherein humidifying the flow further comprises supplying water to the flow of breathable gas by wicking water from the supply of water.

28. A method according to claim 27, wherein wicking water from the supply of water comprises providing a wicking element in contact with the supply of water.

29. A method according to claim 28, wherein the wicking element extends into the flow before the supply of water and/or the flow after the supply of water.

30. A method according to claim 28, further comprising adjusting an amount of the wicking element in contact with the supply of water.

31. A method according to claim 28, wherein the wicking element surrounds at least a portion of the heating element.

32. A method according to claim 26, further comprising, before and/or after generating the flow of breathable gas, supplying power to the heating element.

33. A method according to claim 32, wherein the power supplied to the heating element heats the heating element to a temperature sufficient to kill bacteria and/or disinfect a wicking element.

34. A method according to claim 32, wherein the power supplied to the heating element heats a wicking element to a temperature of about 45°-65° C. for about 5-60 minutes.

35. A method according to claim 34, wherein the temperature of the wicking element is raised to about 60° C. for about 5 minutes.

36. A method according to claim 34, wherein the temperature of the wicking element is raised to about 45° C. for about 15 minutes.

37. A humidifier, comprising:
a tub to contain a supply of water;
an inlet to receive a flow of breathable gas, the inlet configured to direct the flow over the supply of water to humidify the flow;
an outlet connectable to a conduit;
a wicking element provided in the tub; and
a heating element extending from the inlet to the outlet, wherein the heating element is configured to contact the supply of water.

38. A humidifier according to claim 37, wherein the wicking element extends from the tub toward the inlet and/or the outlet.

39. A humidifier according to claim 37, wherein the heating element comprises at least one resistive wire having a first end and a second end; an insulating layer between the first and second ends; and an outer coating surrounding the at least one resistive wire and the insulating layer.

40. A humidifier according to claim 39, wherein the at least one resistive wire comprises two resistive wires that are electrically connected.

41. A humidifier according to claim 39, wherein the at least one resistive wire comprises a ribbon wire.

42. A humidifier according to claim 38, wherein the wicking element is provided around at least a portion of the heating element.

43. A humidifier according to claim 37, wherein the wicking element comprises a woven material, a thread, or a hygroscopic sponge material.

44. A humidifier according to claim 37, further comprising a support in the tub to support the wicking element.

45. A humidifier according to claim 44, wherein the support is a tubular support and the wicking element is provided on an outer surface of the tubular support.

46. A humidifier according to claim 45, wherein the heating element is provided around the tubular support.

47. A humidifier according to claim 44, wherein the support is configured to selectively vary the amount of the wicking element exposed to the flow of breathable gas.

48. A humidifier according to claim 37, further comprising a second heating element to heat the tub.

49. A humidifier according to claim 38, further comprising a power supply and controller configured to supply and control power to the heating element.

50. A humidifier according to claim 49, wherein the heating element comprises a plurality of segments or zones.

51. A humidifier according to claim 50, wherein the power supply and controller is configured to supply and control power independently to each segment or zone.

52. A humidifier according to claim 49, wherein the power supply and controller is configured to supply power to the heating element prior to and/or after operation of the flow generator to generate the flow of breathable gas.

53. A humidifier according to claim 52, wherein the power supply and controller is configured to supply power to the heating element so that the heating element is heated to a temperature sufficient to kill bacteria and/or disinfect the wicking element.

54. A humidifier according to claim 52, wherein the power supply and controller is configured to heat the wicking element to a temperature of about 45°-65° C. for about 5-60 minutes.

55. A humidifier according to claim 54, wherein the power supply and controller is configured to heat the wicking element to about 60° C. for about 5 minutes.

56. A humidifier according to claim 54, wherein the power supply and controller is configured to heat the wicking element to about 45° C. for about 15 minutes.

57. An apparatus for delivering breathable gas to a patient, comprising:
a flow generator to generate a flow of breathable gas;
a humidifier chamber to contain a supply of water;
a first flow path to deliver the flow of breathable gas from the flow generator to the humidifier chamber;
a second flow path to deliver the flow of breathable gas from the humidifier chamber to a patient interface; and
a flat wire heating element provided at least in the humidifier chamber.

58. An apparatus according to claim 57, wherein the heating element is further provided in the first flow path and/or the second flow path.

59. An apparatus according to claim 57, wherein the flat wire is formed of an alloy.

60. An apparatus according to claim 59, wherein the alloy is a nickel chrome alloy, or a nickel chrome iron alloy.

61. An apparatus according to claim 59, wherein percentages of each metal in the alloy are selected to provide a predetermined maximum power and a predetermined maximum temperature of the flat wire.

62. An apparatus according to claim 57, wherein the flat wire is formed of metal.

63. An apparatus according to claim 62, wherein the metal is copper or silver.

64. An apparatus according to claim 57, wherein the flat wire is formed of a positive thermal coefficient material.

65. An apparatus according to claim 64, wherein the positive thermal coefficient material is selected so that a maximum temperature of the flat wire may be attained upon application of a constant voltage.

66. An apparatus according to claim 65, wherein the maximum temperature is about 70° C.

67. An apparatus according to claim 57, wherein the heating element comprises a polymer thin film comprising a circuit.

68. An apparatus according to claim 67, wherein the polymer thin film comprises polyimide, silicone rubber, polycarbonate, polyester, polypropylene or PTFE.

69. An apparatus according to claim 67, wherein the circuit is printed on the polymer thin film.

70. An apparatus according to claim 69, wherein the circuit is printed by etching or vacuum deposition.

71. An apparatus according to claim 67, wherein the heating element comprises a second polymer thin film over the circuit.

72. An apparatus according to claim 67, wherein the circuit comprises electrically conductive ink.

73. An apparatus according to claim 72, wherein the electrically conductive ink comprises silver ink, carbon ink, or a combination thereof.

74. An apparatus according to claim 67, wherein the circuit comprises a wire, a ribbon, and/or a resistive conductor.

75. An apparatus according to claim 67, wherein the circuit comprises a positive thermal coefficient material.

76. An apparatus according to claim 67, wherein the circuit comprises a negative thermal coefficient material.

77. An apparatus according to claim 67, wherein the heating element comprises a plurality of circuits.

78. An apparatus according to claim 77, wherein the plurality of circuits are provided in series and/or parallel.

79. An apparatus according to claim 57, wherein the heating element comprises a polymer thin film wrapped by a wire.

80. An apparatus according to claim 57, wherein the heating element has a width of about 1-10 mm.

81. An apparatus according to claim 57, wherein the heating element has a width of about 5 mm.

82. An apparatus according to claim 57, wherein the heating element has a thickness of about 0.1 to 1 mm.

83. An apparatus according to claim 57, wherein the heating element has a thickness of about 0.2 to 0.5 mm.

84. An apparatus according to claim 57, wherein at least a portion of the heating element is covered by an insulating material.

85. An apparatus according to claim 57, wherein at least a portion of the heating element is covered by a wicking element.

86. An apparatus according to claim 57, further comprising a power supply and controller configured to apply a voltage to the heating element.

87. A method of delivering a flow of breathable gas to a patient, comprising:
generating a flow of breathable gas; and
humidifying the flow by passing the flow over a supply of water, wherein humidifying the flow comprises heating the supply of water and/or the flow with a heating element in thermal contact with the water and/or the flow before passing the supply of water, the flow over the supply of water, and/or the flow after passing the supply of water, the heating element being a continuous strip in direct contact with the flow upstream of the supply of water and in direct contact with the flow downstream of the supply of water; and
controlling a voltage applied to the heating element to adjust a temperature of the heating element and the humidity of the flow.

88. A method according to claim 87, wherein the heating element comprises a flat, elongate heating element.

89. A method according to claim 87, wherein the heating element has a width of about 1-10 mm.

90. A method according to claim 87, wherein the heating element has a width of about 5 mm.

91. A method according to claim 87, wherein the heating element has a thickness of about 0.1 to 1 mm.

92. A method according to claim 88, wherein the heating element has a thickness of about 0.2 to 0.5 mm.

93. A method according to claim 87, wherein the voltage is controlled to provide a relative humidity greater than 50%.

94. A method according to claim 87, wherein humidifying the flow further comprises wicking water from the supply of water.

95. A tube for use in delivering a flow of breathable gas to a patient comprising a circuit comprising electrically conductive ink provided on an inner surface and/or an outer surface, the tube defining the first and/or second flow path of the apparatus of claim 57.

96. A tube according to claim 95, wherein the electrically conductive ink is carbon ink, silver ink, or a combination thereof.

97. A tube according to claim 95, wherein the electrically conductive ink is provided in a predetermined pattern configured to provide a predetermined heating pattern when a predetermined voltage is applied to the circuit.

98. A method of disinfecting an apparatus for delivering breathable gas to a patient comprising a flow generator to generate a flow of breathable gas; a humidifier chamber to contain a supply of water; a first flow path to deliver the flow of breathable gas from the flow generator to the humidifier chamber; a second flow path to deliver the flow of breathable gas from the humidifier chamber to a patient interface; and a flat, elongate heating element provided in the humidifier chamber, the first flow path, and/or the second flow path, the method comprising:
  prior to and/or after operation of the flow generator, heating the heating element to a temperature sufficient to kill bacteria and/or disinfect a wicking element.

99. An apparatus for delivering breathable gas to a patient, comprising:
  a flow generator to generate a flow of breathable gas;
  a humidifier chamber to contain a supply of water;
  a first flow path to deliver the flow of breathable gas from the flow generator to the humidifier chamber;
  a second flow path to deliver the flow of breathable gas from the humidifier chamber to a patient interface;
  a wicking element provided at least in the humidifier chamber;
  a heating element extending through the first flow path, the humidifier chamber and into the second flow path; and
  a power supply and control configured to supply and control power to the heating element, wherein the power supply and control is configured to supply and control power to the heating element prior to and/or after operation of the flow generator to heat the heating element to a temperature sufficient to kill bacteria and/or disinfect the wicking element.

100. An apparatus according to claim 1, wherein the heating element comprises:
  at least two opposing surfaces;
  an insulating layer, at least a portion of the insulating layer being positioned between the at least two opposing surfaces; and
  an outer coating surrounding the at least two opposing surfaces.

101. An apparatus according to claim 100, wherein the at least two opposing surfaces are part of a single resistive wire folded over upon itself.

102. An apparatus according to claim 101, wherein the insulating layer surrounds the at least two opposing surfaces.

103. An apparatus according to claim 102, wherein the insulating layer includes opposing surfaces.

104. An apparatus according to claim 103, wherein the at least two opposing surfaces of the single resistive wire and the insulation layer are encapsulated by a protective coating.

105. An apparatus according to claim 100, wherein the at least two opposing surfaces are surfaces of at least two different resistive wires, the at least two different resistive wires being electrically connected.

106. An apparatus according to claim 105, wherein the insulating layer surrounds the at least two opposing surfaces.

107. An apparatus according to claim 106, wherein the insulating layer includes opposing surfaces.

108. An apparatus according to claim 107, wherein the at least two opposing surfaces of the at least two different resistive wires and the insulation layer are encapsulated by a protective coating.

* * * * *

UNITED STATES PATENT AND TRADEMARK OFFICE
CERTIFICATE OF CORRECTION

PATENT NO. : 8,459,259 B2  
APPLICATION NO. : 12/669889  
DATED : June 11, 2013  
INVENTOR(S) : Klasek et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 564 days.

Signed and Sealed this
Eighth Day of September, 2015

Michelle K. Lee
*Director of the United States Patent and Trademark Office*